(12) United States Patent
Schell et al.

(10) Patent No.: US 10,143,858 B2
(45) Date of Patent: Dec. 4, 2018

(54) NORMAL TISSUE SPARING IN RADIATION THERAPY TREATMENT PLANNING USING PRIORITIZATION FOR OPTIMIZING TISSUE INDICES

(71) Applicant: Brainlab AG, Munich (DE)

(72) Inventors: Stefan Schell, Munich (DE); Claus Promberger, Pfaffenhofen (DE); Robert Grummt, Munich (DE); Andreas Schaetti, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/560,737

(22) PCT Filed: Oct. 14, 2015

(86) PCT No.: PCT/EP2015/073811
§ 371 (c)(1),
(2) Date: Sep. 22, 2017

(87) PCT Pub. No.: WO2017/063691
PCT Pub. Date: Apr. 20, 2017

(65) Prior Publication Data
US 2018/0093109 A1    Apr. 5, 2018

(51) Int. Cl.
*A61B 34/10* (2016.01)
*A61N 5/10* (2006.01)
(Continued)

(52) U.S. Cl.
CPC ......... *A61N 5/1071* (2013.01); *A61N 5/1031* (2013.01); *A61N 5/1038* (2013.01);
(Continued)

(58) Field of Classification Search
CPC ........... A61B 6/00; A61B 6/52; A61B 6/5211; A61B 6/5217; A61B 6/5229; A61B 34/00;
(Continued)

(56) References Cited

U.S. PATENT DOCUMENTS

2006/0256915 A1    11/2006   Otto et al.
2008/0008291 A1    1/2008    Alakuijala et al.
(Continued)

FOREIGN PATENT DOCUMENTS

EP    2038010 B1    9/2013

OTHER PUBLICATIONS

European Patent Office, International Search Report and Written Opinion for corresponding PCT/2015073811 dated Jun. 14, 2016, pp. 1-10.

(Continued)

*Primary Examiner* — Anastasia Midkiff
(74) *Attorney, Agent, or Firm* — Tucker Ellis LLP

(57) ABSTRACT

Disclosed is a computer-implemented medical data processing method for determining a dose distribution for use in a medical procedure involving irradiation of an anatomical structure of a patient's body with ionizing radiation. A processor acquires medical image data describing a medical image of the anatomical structure. The processor acquires dose distribution data describing an irradiation dose distribution spatially defined in the reference system of the medical image of the anatomical structure. Prioritization data is determined that describes, for each image unit of the medical image describing non-target tissue, a priority of that image unit for consideration during an optimization of the irradiation dose distribution described by the dose distribution data. Based on the dose distribution data and the prioritization data, changed dose distribution data is determined that describes a changed irradiation dose distribution spatially defined in the reference system of the medical image of the anatomical structure.

16 Claims, 3 Drawing Sheets

(51) Int. Cl.
  *G01T 7/00* (2006.01)
  *G06T 7/00* (2017.01)
  *A61B 6/00* (2006.01)

(52) U.S. Cl.
  CPC .......... *G06T 7/0014* (2013.01); *A61B 6/5217* (2013.01); *A61B 34/10* (2016.02); *A61B 2560/0266* (2013.01); *G01T 7/005* (2013.01); *G06T 2207/20004* (2013.01); *G06T 2207/20221* (2013.01); *G06T 2207/30004* (2013.01)

(58) Field of Classification Search
  CPC ... A61B 34/10; A61B 34/107; A61B 2560/00; A61B 2560/02; A61B 2560/0266; A61N 5/00; A61N 5/10; A61N 5/103; A61N 5/1031; A61N 5/1038; A61N 5/1039; A61N 5/1048; A61N 5/1064; A61N 5/1071; A61N 5/1074; G01T 1/00; G01T 1/29; G01T 1/2914; G01T 7/00; G01T 7/005; G06K 9/36; G06K 9/46; G06T 5/40; G06T 7/00; G06T 7/0002; G06T 7/0012; G06T 7/0014; G06T 2210/44; G06T 2211/40; G06T 2207/00; G06T 2207/10072; G06T 2207/10081; G06T 2207/10116; G06T 2207/20; G06T 2207/20004; G06T 2207/20021; G06T 2207/20228; G06T 2207/30; G06T 2207/30004

See application file for complete search history.

(56) References Cited

U.S. PATENT DOCUMENTS

| | | |
|---|---|---|
| 2013/0324784 A1 | 12/2013 | Fredriksson |
| 2014/0275706 A1 | 9/2014 | Dean et al. |
| 2014/0350322 A1* | 11/2014 | Schulte ................ A61N 5/1039 600/1 |
| 2016/0287906 A1* | 10/2016 | Nord ...................... A61N 5/103 |

OTHER PUBLICATIONS

Snyder, IMRT Planning Basics, AAMD Student Webinar, Varian Medical System, Department of Radiation Oncology, Mar. 12, 2014, pp. 1-62.

* cited by examiner

NORMAL TISSUE SPARING IN RADIATION THERAPY TREATMENT PLANNING USING PRIORITIZATION FOR OPTIMIZING TISSUE INDICES

RELATED APPLICATION DATA

This application is a national phase application of International Application No. PCT/EP2015/073811 filed Oct. 14, 2015 published in the English language.

The present invention is directed to a computer-implemented method for determining a dose distribution for use in a medical procedure (for example radiotherapy or radiosurgery) involving irradiation of an anatomical structure of a patient's body with ionising radiation, a corresponding computer program, a non-transitory program storage medium storing such a program and a computer running the computer program, as well as a system for controlling an irradiation therapy device comprising a database and such a computer.

TECHNICAL BACKGROUND

When planning a dose distribution to be applied to a patient during radiotherapy or radiosurgery, it is generally desirable to avoid associating high doses with tissue outside the target region. A known approach disclosed in EP 2 038 010 B1 includes penalizing irradiation of normal tissue based on the distance of corresponding voxels to the target region in a medical image of the anatomical setting. This, however, does not allow for selective optimization of tissue indices which are frequently used to describe the quality of a planned dose distribution.

An object of the invention therefore is to provide a method of determining a dose distribution which results in an optimized quality measure for the dose distribution regarding irradiation of tissue lying outside the target region.

Aspects of the present invention, examples and exemplary steps and their embodiments are disclosed in the following. Different advantageous features can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses analysing medical image data and an associated predetermined irradiation dose distribution for the contribution of voxels representing normal tissue and their associated dose defined by the irradiation dose distribution to a tissue index describing the quality of the irradiation dose distribution with regard to the dose applied to normal tissue. On the basis of that contribution, the voxels representing normal tissue are each assigned a priority with which the voxel will be included in an optimization procedure for optimizing the irradiation dose distribution to minimise irradiation of normal tissue as far as possible.

General Description of the Present Invention

In this section, a description of the general features of the present invention is given for example by referring to possible embodiments of the invention.

In general, the invention reaches the aforementioned object by providing, in a first aspect, a computer-implemented method for determining a dose distribution for use in a medical procedure (for example radiotherapy or radiosurgery) involving irradiation of an anatomical structure of a patient's body with ionising radiation. The method comprises executing, on at least one processor of at least one computer, the following exemplary steps which are executed by the at least one processor.

In a (for example first) exemplary step, medical image data is acquired which describes (for example, represents or defines) a medical image of the anatomical structure, wherein the anatomical structure comprises both a target region (comprising for example tumour tissue) which defines a target of the irradiation and non-target tissue, wherein irradiation of the non-target tissue shall be avoided. The anatomical structure can be located in any body part and can comprise at least one of soft tissue (such as skin, brain matter or an internal organ) and hard tissue (such as bone tissue or cartilage). The non-target tissue is for example defined to lie in a spherical shell defined in the medical image around the target region. The non-target comprises (specifically, consists of) normal tissue which is tissue within the patient that is not supposed to be irradiated but still receives a certain amount of dose nevertheless. This unwanted tissue irradiation exists because it is technically not possible to have dose only in the target region (the planning treatment volume PTV) and no dose anywhere else. By definition, normal tissue is used to refer to tissue outside the PTV. The non-target tissue is generally disjoint from the target region and may but need not necessarily comprise specific risk regions (organs-at-risk, i.e. organs which must not be irradiated during the medical procedure if a particular risk to the patient is to be avoided). The non-target tissue is for example normal tissue. The medical image data may be patient-specific and have been generated by applying a medical imaging modality (such as magnetic resonance tomography or computed x-ray tomography, conventional x-ray imaging or ultrasound imaging) to the specific patient's anatomical structure. Alternatively, the medical imaging data may not be patient-specific, for example if the medical image data comprises (specifically, consists of) atlas data describing (for example, representing or defining) an image-based model of the anatomical structure which has been generated for example from medical images generated for a population of patients. The medical image data in one example is three-dimensional image data but may alternatively be two-dimensional image data (for example, if it has been generated by conventional x-ray imaging).

In a further (for example second) exemplary step, dose distribution data is acquired which describes (for example, represents or defines) an irradiation dose distribution which is spatially defined in the reference system (coordinate system) of the medical image of the anatomical structure. The dose distribution data is for example predetermined (i.e. the irradiation dose distribution is for example predetermined) and has been generated before execution of the disclosed method starts. However, the irradiation dose distribution may also be predetermined in the sense that it is the output of an iteration of the disclosed method, i.e. that it is the result of an optimization step. "Predetermined" in this context therefore means that the irradiation dose distribution is not calculated in this step but read as an input data set, which may also be input from a stored result of previous iteration of the optimization algorithm described below.

In a further (for example third) exemplary step, prioritization data is determined which describes (for example, represents or defines), for each image unit of the medical image describing (for example representing or defining) non-target tissue, a priority of that image unit for consideration during an optimization of the irradiation dose distribution described by the dose distribution data. The prioritization data is determined based on the medical image data and the dose distribution data. The term of image unit denotes a pixel or voxel, respectively, depending on the dimensionality of the medical image data.

The priority defines an influence of the dose values associated with the image units having the respective priority on determining a desired changed irradiation dose distribution by applying an optimization algorithm. The priority associated with an image unit defines for example the influence of that image unit on a cost function to be optimized by the aforementioned optimization. The influence (and therefore also the priority) is represented by for example a numeric value which correlates with the contribution of the image unit to the optimization result, wherein for example irradiation dose values assigned to image units representing non-target tissue and associated with an irradiation dose of more than a prescribed dose are considered to have a higher influence on determining the desired changed irradiation dose distribution. The prescribed dose defines a dose which shall be administered to the target region and generally is predetermined and used as an input parameter to the disclosed method.

In a first embodiment of this step, tissue index contribution data is acquired based on the medical image data such as by image analysis of the medical image data. The tissue index contribution data describes (for example, represents or defines), for each image unit of the medical image of the anatomical structure describing non-target tissue, a contribution of the irradiation dose assigned to that image unit to at least one tissue index describing the quality of the irradiation dose distribution. The contribution is defined for example based on prior knowledge such as expert knowledge applied by a physician or a medical physicist. The prioritization data is in this first embodiment determined further based on the tissue index contribution data.

The aforementioned tissue index may be at least one of the conformity index and the gradient index which are associated with the dose distribution data and the medical image data. The conformity index CI is defined for example as CI=(volume of the target region*volume of the target region or the non-target tissue having an assigned irradiation dose larger than 100% of the prescribed dose)/(volume of the target region having an assigned irradiation dose larger than 100% of the prescribed dose)$^2$. The gradient index GI is defined for example as GI=(volume of the target region or the non-target tissue having an assigned irradiation dose larger than 50% of the prescribed dose)/(volume of the target region or the non-target tissue having an assigned irradiation dose larger than 100% of the prescribed dose). In the expressions for CI and GI, * is the arithmetic operator of multiplication and/is the arithmetic operator of division.

For example, an image unit associated with a dose representing a predetermined percentage of a prescribed dose is determined to have an effect on either the CI or the GI or neither the CI nor the GI. Depending on the determined effect, the image unit is assigned a numeric value representing the priority for that image unit.

In a second embodiment of this step, the prioritization data is determined based on determining (for example, by determining) the result of $|D_i^{desired} - D_i^{actual}(\omega)|$ or $(D_i^{desired} - D_i^{actual}(\omega))^2$. $D_i^{desired}$ is a desired irradiation dose to be applied to the non-target tissue represented by the i-th image unit, and $D_i^{actual}(\omega)$ is the irradiation dose to be applied to the non-target tissue represented by the i-th image unit and described by the dose distribution data and is dependent on the machine configuration $\omega$. $D_i^{desired}$ is set such that image units associated with a higher priority are associated with a higher value of $|D_i^{desired} - D_i^{actual}(\omega)|$ or $(D_i^{desired} - D_i^{actual}(\omega))^2$, respectively (i.e. depending on whether the result of $|D_i^{desired} - D_i^{actual}(\omega)|$ or $(D_i^{desired} - D_i^{actual}(\omega))^2$ is used as a basis for determining the prioritization data). For example for a high-priority image unit $D_i^{desired}$ is set to $D_i^{desired} = a_i D_i^{actual}(\omega)$ and for a lower-priority image unit $D_i^{desired}$ is set to $D_i^{desired} = b_i D_i^{actual}(\omega)$, and $a_i$, $b_i$ are numeric values with $0 < a_i < b_i < 1$. Therefore, $D_i^{desired}$ is set for the i-th image unit such that the priority is reflected in the cost function.

In a further (for example fourth) exemplary step, changed dose distribution data is determined which describes (for example, represents or defines) a changed irradiation dose distribution which is spatially defined in the reference system of the medical image of the anatomical structure. The changed dose distribution data is determined based on the dose distribution data and the prioritization data. The changed irradiation dose distribution is for example an optimized irradiation dose distribution (such as an optimization of the irradiation dose distribution described by the dose distribution data). Furthermore, the changed irradiation dose distribution is comprised in the output of at least a step (i.e. at least one incremental step or in the final result) of an optimization algorithm having the dose distribution data and the prioritization data as an input. For example, the tissue index is the conformity index and the gradient index and determining the changed dose distribution data involves minimising the conformity index and the gradient index in order to optimize the predetermined irradiation dose distribution.

For example, the changed dose distribution data is determined based on (specifically, by) minimising a cost function $f(\omega) = f_0(\omega) + f_1(\omega)$. $f_1(\omega)$ describes (for example, represents or defines) the part of the cost function for the non-target tissue and is defined as $f_1(\omega) = \Sigma_i p_i [D_i^{desired} - D_i^{actual}(\omega)]^2$. $f_0(\omega)$ describes (for example, represents or defines) the part of the cost function for parts of the anatomical structure other than the non-target tissue. Furthermore, $f_0(\omega)$ may for example describe (for example, represent or define) irradiation parameters like the number of monitor units or the total movement of all collimator leaves of a collimator of an irradiation device usable for irradiating the anatomical structure with ionising treatment radiation. $\omega$ is a parameter defining the machine configuration of an irradiation apparatus to be used for irradiating the anatomical structure, $p_i$ is a numeric value defining the priority of the i-th image unit describing non-target tissue and for example assigned to the i-th image unit based on prior knowledge, $D_i^{desired}$ is a desired irradiation dose to be applied to the non-target tissue represented by the i-th image unit, and $D_i^{actual}(\omega)$ is the irradiation dose to be applied to the non-target tissue represented by the i-th image unit and described by the dose distribution data and is dependent on the machine configuration $\omega$, where the machine configuration is defined by for example at least one of: the table angles of a table for placement of the patient when conducting the medical procedure, the vertical angle of a gantry of an irradiation device for irradiating the anatomical structure with the ionising radiation, the collimator angle of a collimator (for example, a multi-leaf collimator) for collimating the beam of ionising radiation to be emitted by the irradiation device, a jaw configuration of the irradiation device (the jaw is a for example rectangular additional collimator which is coarser than the multi-leaf collimator), and the monitor units per control point. A monitor unit is the smallest unit of photon fluence that a radiation therapy device can produce. It is linked to a certain dose at a certain depth for a certain aperture size of the radiation therapy device in a certain quality assurance device. Monitor units are not directly linked to the dose in patients because the aperture can be highly modulated. Large monitor units are usually associated with small apertures and therefore more leakage and stray irradiation of the patient.

On the basis of the changed dose distribution data, treatment plan data describing (for example, representing or defining) a treatment plan for conducting the medical procedure is determined in one example of the disclosed method. The treatment plan defines further details of the medical procedure to be carried out on the patient such as number of irradiation fractions and time intervals between fractions.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the program storage medium according to the third aspect.

In a fifth aspect, the invention is directed to a system for controlling an irradiation therapy device for use in a medical procedure involving irradiation of an anatomical structure with ionising radiation. The system comprises:
a) the at least one computer according to the fourth aspect;
b) at least one electronic data storage device storing at least one database comprising the medical image data and the dose distribution data,
   wherein the at least one computer is operably coupled to the at least one database for acquiring, from the at least one database, the medical image data and the dose distribution data; and
c) the irradiation therapy device which is configured to emit a beam of ionising treatment radiation,
   wherein the computer is operatively coupled to the irradiation therapy device so as to effect emission of the treatment radiation by the irradiation therapy device based on the changed dose distribution data.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The present invention relates to the field of controlling a treatment beam. The treatment beam treats body parts which are to be treated and which are referred to in the following as "treatment body parts". These body parts are for example parts of a patient's body, i.e. anatomical body parts.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to controlling beams, such as radiation beams, to treat parts of a patient's body, which are therefore also referred to as treatment beams, and the radiation is also called treatment radiation. A treatment beam treats body parts which are to be treated and which are referred to in the following as "treatment body parts". These body parts are for example parts of a patient's body, i.e. anatomical body parts or the above-mentioned anatomical structure. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts" or "non-target tissue". Generally, a treatment beam has to pass through outside body parts in order to reach and so pass through the treatment body part, specifically the target region.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 shows the flow of the steps of the disclosed method. In step S1, the medical image data is acquired as input data, by reading (loading) for example from a database containing a repository of patient-specific images or image-based atlas data. In subsequent step S2, the dose distribution data is acquired as input data for example by reading (loading) a dose distribution which has previously been determined for a specific patient or an atlas representation of the anatomical structure and stored for use e.g. in this method. This predetermined dose distribution is a dose distribution which shall be optimized by the disclosed method. Step S3 involves determining (for example, computing) the prioritization data as an output. Step S4 uses the dose distribution data and the previously determined prioritization data as an input for determining (for example calculating) the changed dose distribution data.

FIG. 2 illustrates the logic of assigning the priority for each image unit (voxel). The medical image data is analysed for normal tissue in order to gather information about the position of the normal tissue in the medical image. This information is acquired as normal tissue data. Also, the dose distribution data is acquired. It is then analysed which actual dose described by the dose distribution data is assigned to which voxel describing normal tissue in the medical image. The dose thus determined is compared to previously acquired predetermined information describing (for example defining) the value of a prescribed dose. If that comparison results in that the actual dose associated with a specific voxel is above 100% of the prescribed dose, it is determined that the associated voxel and this actual dose have an effect on the conformity index CI which should be optimized with a higher priority than the gradient index of an optimized dose distribution. That voxel is therefore assigned a high (in this case, the highest) priority, i.e. is set first among the three possibilities of FIG. 2 for prioritizing the voxels. If the comparison results in that the actual dose associated with a specific voxel is in an interval from 50% to 100% of the prescribed dose, it is determined that the associated voxel and this actual dose have an effect on the gradient index GI, which shall in the example of FIG. 2 be optimized with medium priority. That voxel is therefore assigned a medium priority, i.e. is set second among the three possibilities of FIG. 2 for prioritizing the voxels. If the comparison results in that the actual dose associated with a specific voxel is less than 50% of the prescribed dose, it is determined that the associated voxel and this actual dose have no effect on both the conformity index CI and the gradient index GI. Since it is an aim of the disclosed method to optimize the CI and the GI, that voxel is therefore assigned a low priority (in the example of FIG. 2, the lowest priority), i.e. is set third among the three possibilities of FIG. 2 for prioritizing the voxels. The priority assigned to each voxel is then considered for running a next iteration of the optimization algorithm on the medical image data and the dose distribution data. The optimization algorithm ("optimizer") is then re-run, and the method continues with re-analysing the dose of each voxel in normal tissue until an exit criterion for exiting the optimization is fulfilled.

FIG. 3 shows how determining the result of $|D_i^{desired} - D_i^{actual}(\omega)|$ or $(D_i^{desired} - D_i^{actual}(\omega))^2$ leads to assigning a priority to each voxel. In the dose volume histogram of normal tissue shown in FIG. 3, classes are defined for voxels having assigned an actual dose d lying in an interval ranging from 0% of the prescribed dose to less than 50% of the prescribed dose, from 50% to 100% of the prescribed dose and greater than 100% of the prescribed dose. A difference ("distance") is determined between the actual dose and the desired dose ("dose objective") for each voxel, and the larger this difference is, the higher the priority is set for that voxel specifically within the miscellaneous regime ("misc regime"), the gradient index regime ("GI regime") and the conformity index regime ("CI regime") applicable to the respective voxel due to lying in one of the aforementioned dose classes.

Figure 1:
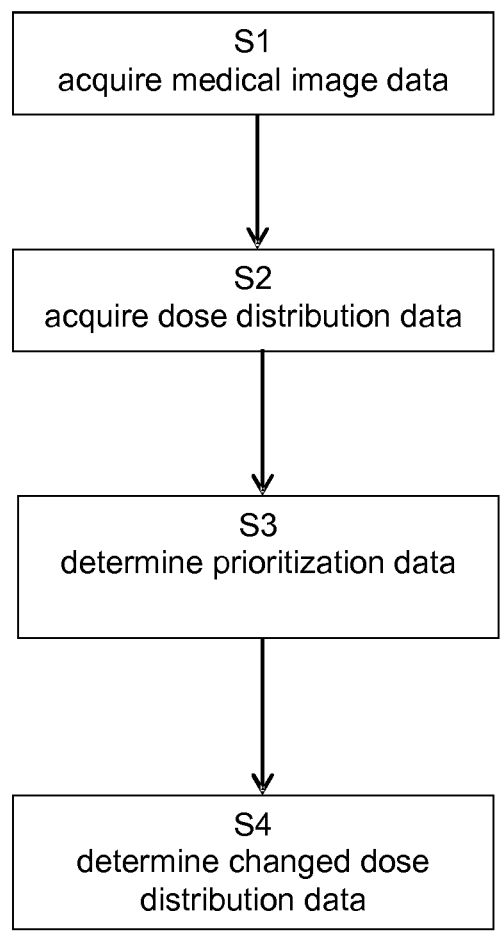
FIG. 1 is a flow diagram showing the steps of the disclosed method.
Figure 2:
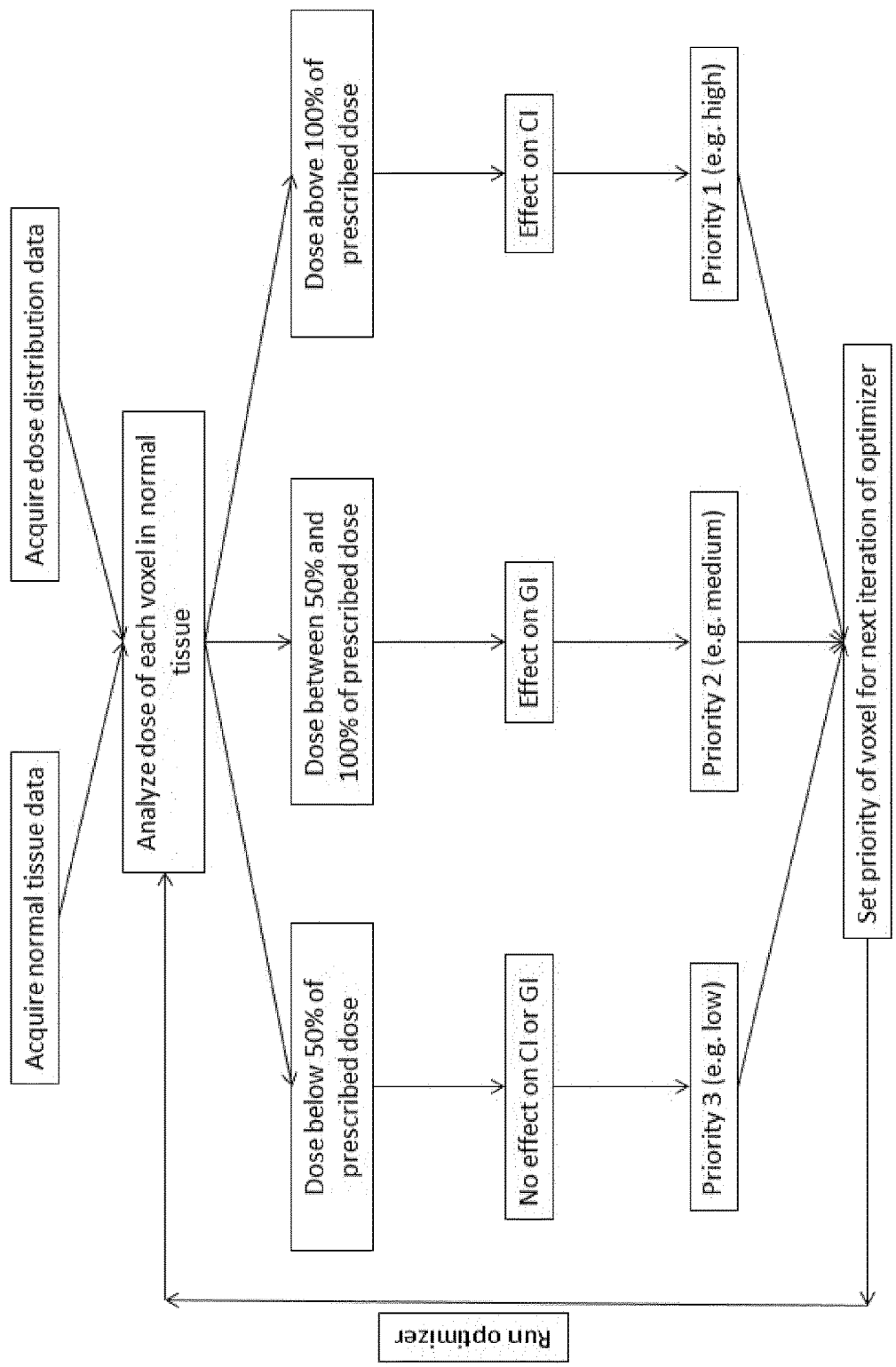
FIG. 2 is a chart illustrating assignment of priorities to image units based on their assigned actual dose.
Figure 3:
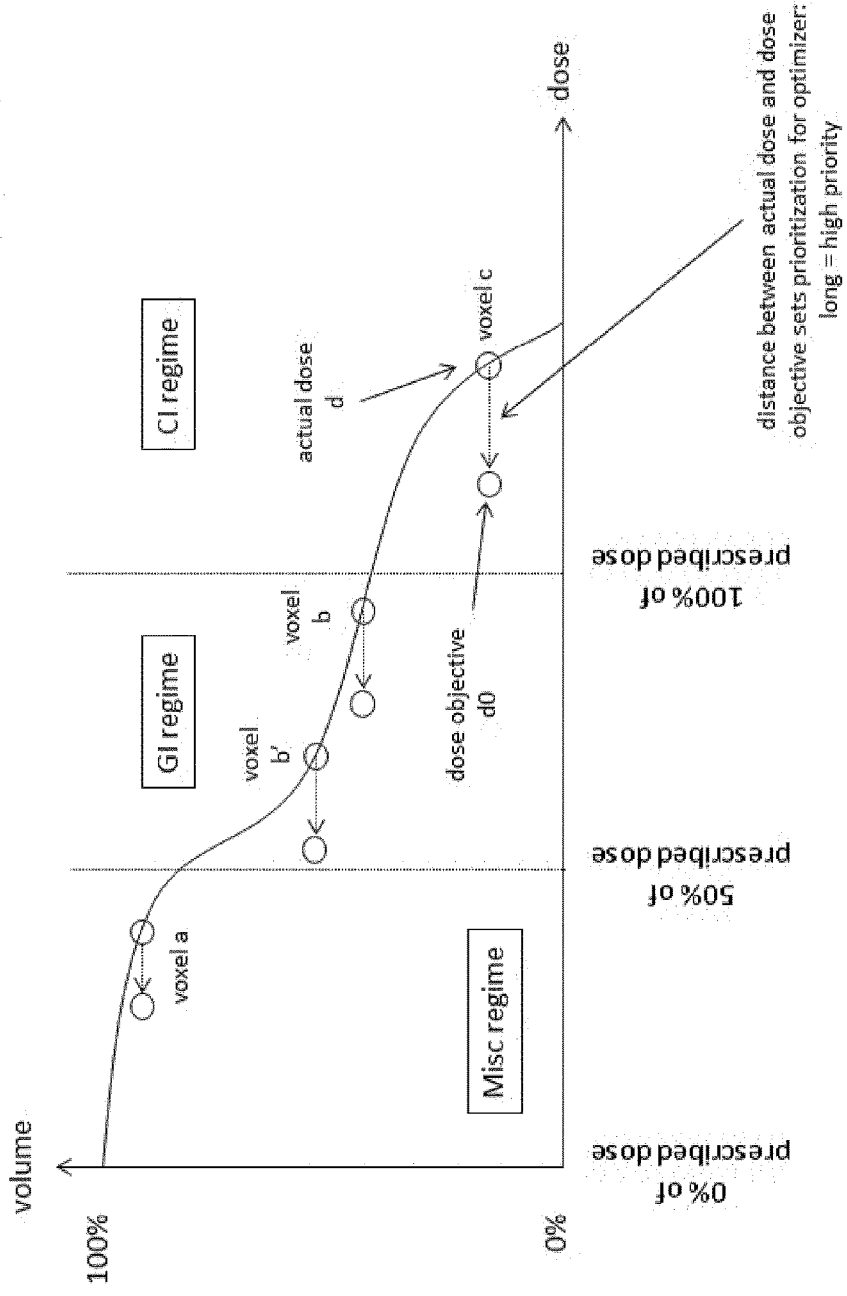
FIG. 3 shows assigning a priority to an imaging unit depending on the difference between the actual dose and the desired dose assigned to that image unit.

The classes defining the percentage of the prescribed dose for determining the priority to be assigned to a specific voxel in the cases of FIGS. 2 and 3 are three. However, other or more classes may be used for implementing the method. In particular, more than three priorities may be used, for example if the classes are defined more finely by choosing smaller percentage intervals between class boundaries.

In the example of FIG. 3, voxel c has an actual dose d. If we do not want to have any dose in this anatomical structure one could set the dose objective (desired dose) for this voxel to zero. This tells the optimizer to try to achieve zero actual dose for this voxel. However, having zero actual dose is often technically not possible. Therefore, it is better to ask for a more realistic dose objective. In the drawing we chose d0 which is not zero, however smaller than d. The reason why we should not ask for zero dose is that asking for unrealistic doses would mislead the optimization algorithm because it would spend all its degrees of freedom while trying to achieve an unrealistic goal. Therefore, it is important to tell the optimization algorithm what a realistic goal of the optimization is, thus it is advisable not to ask for things which are not possible, and also not to ask for things which are not required. Additionally, there needs to be a clear prioritization of goals. Otherwise the optimization result is potentially wasting possibilities.

Therefore, the disclosed method looks at the non-zero actual dose of each voxel in the normal tissue and assigns a non-zero dose objective for the next optimization step. This dose objective is always lower than the actual dose but not zero.

The disclosed method assigns dose objectives depending on the voxel's contribution to CI and/or GI. For example, if the voxel is located in the CI regime (voxel c), a dose objective d0 is placed a certain distance to the left (lower dose) of the actual voxel dose d. As described above, the distance between the actual dose and the dose objective (i.e. d−d0) affects the prioritization. Longer distances mean higher priority. Thus, points in the GI regime (voxel b, or voxel b') or misc regime (voxel a) will receive objectives which are not as far away from the actual voxel dose because these regimes are considered less important. As explained above, the dose objectives are used by the optimizer to steer the result into the required direction.

After each optimization step a new dose volume histogram representation of the current dose distribution is calculated.

The disclosed method allows the prioritization of one index over another (e.g. CI over GI). Therefore, it is possible to use the degrees of freedom of the optimization problem to achieve a result that, for example, primarily has a good CI and only secondarily has a good GI. Older approaches (e.g. the one disclosed in EP 2 038 010 B1) cannot incorporate this common clinical wish into the optimization problem.

The invention claimed is:

1. A method for determining a dose distribution for use in a medical procedure involving irradiation of an anatomical structure of a patient's body with ionizing radiation, the method executing on at least one processor of at least one computer, and comprising:
  a) acquiring, at the at least one processor, medical image data describing a medical image of the anatomical structure, the medical image comprising a plurality of image units, wherein the anatomical structure comprises both a target region which defines a target of the irradiation and non-target tissue;
  b) acquiring, at the at least one processor, dose distribution data describing an irradiation dose distribution of the anatomical structure, as spatially defined in a reference system of the medical image;
  c) acquiring, at the at least one processor and based on the medical image data, tissue index contribution data, wherein said tissue index contribution data describes, for each image unit of the medical image describing non-target tissue, a contribution of the irradiation dose assigned to that image unit to at least one tissue index, said tissue index describing a quality of the irradiation dose distribution, wherein said at least one tissue index is at least one of:
    i) a conformity index (CI) which is associated with the dose distribution data and the medical image data and which is defined as CI=(volume of the target region*volume of the target region or the non-target tissue having an assigned irradiation dose larger than 100% of the prescribed dose)/(volume of the target region having an assigned irradiation dose larger than 100% of the prescribed dose)$^2$, where * is the arithmetic operator of multiplication and/is the arithmetic operator of division; and
    ii) a gradient index GI which is associated with the dose distribution data and the medical image data and which is defined as GI=(volume of the target region or the non-target tissue having an assigned irradiation dose larger than a predetermined percentage of the prescribed dose)/(volume of the target region or the non-target tissue having an assigned irradiation dose larger than 100% of the prescribed dose);
  d) determining prioritization data by the at least one processor, said prioritization data based on the medical image data, the dose distribution data, and the tissue index contribution data, wherein said prioritization data describes, for each image unit describing non-target tissue, a priority of each image unit for consideration during an optimization of the irradiation dose distribution described by the dose distribution data;
  e) determining changed dose distribution data by the at least one processor, said changed dose distribution data based on the dose distribution data and the prioritization data, wherein said changed dose distribution data describes a changed irradiation dose distribution spatially defined in the reference system of the medical image of the anatomical structure, and wherein the changed irradiation dose distribution is comprised in the output of at least a step of an optimization algorithm, said optimization algorithm having the dose distribution data and the prioritization data as an input.

2. The method according to claim 1, wherein the priority defines, for a dose value associated with each image unit, an influence on determining a desired changed irradiation dose distribution by applying the optimization algorithm, and wherein the influence is represented by a numeric value which correlates with the contribution of the image unit to an optimization result.

3. The method according to claim 1, wherein the contribution of the irradiation dose assigned to each image unit is defined based on prior knowledge.

4. The method according to claim 1, wherein the tissue index includes both the conformity index and the gradient index and wherein determining the changed dose distribution data involves minimizing the conformity index and the gradient index.

5. The method according to claim 1,
  wherein the prioritization data is determined, by the at least one processor, based on determining the result of $|D_i^{desired}-D_i^{actual}(\omega)|$ or $(D_i^{desired}-D_i^{actual}(\omega))^2$, where $D_i^{desired}$ is a desired irradiation dose to be applied to the non-target tissue represented by the i-th image unit, and $D_i^{actual}(\omega)$ is the irradiation dose to be applied to the non-target tissue represented by the i-th image unit and described by the dose distribution data and is dependent on a machine configuration $\omega$,
  wherein $D_i^{desired}$ is set such that image units associated with a higher priority are associated with a higher value of $|D_i^{desired}-D_i^{actual}(\omega)|$ or $(D_i^{desired}-D_i^{actual}(\omega))^2$, respectively,
  wherein, for a high-priority image unit, $D_i^{desired}$ is set to $D_i^{desired}=a_i D_i^{actual}(\omega)$ and for a low-priority image unit $D_i^{desired}$ is set to $D_i^{desired}=b_i D_i^{actual}(\omega)$, where $0<a_i<b_i<1$.

6. The method according to claim 1, wherein the changed dose distribution data is determined, by the at least one processor, based on minimizing a cost function $f(\omega)=f_0(\omega)+f_1(\omega)$,
  where $f_1(\omega)$ describes the part of the cost function for the non-target tissue and is defined as $f_1(\omega)=\Sigma_i p_i[D_i^{desired}-D_i^{actual}(\omega)]^2$,
  where $f_0(\omega)$ describes the part of the cost function for parts of the anatomical structure other than the non-target tissue and irradiation parameters,
  where $\omega$ is a parameter defining a machine configuration of an irradiation apparatus to be used for irradiating the anatomical structure,
  where $p_i$ is a numeric value defining the priority of the i-th image unit describing non-target tissue and assigned to the i-th image unit based on prior knowledge,
  where $D_i^{desired}$ is a desired irradiation dose to be applied to the non-target tissue represented by the i-th image unit,
  where $D_i^{actual}(\omega)$ is the irradiation dose to be applied to the non-target tissue represented by the i-th image unit and described by the dose distribution data and is dependent on the machine configuration $\omega$, and
  wherein the machine configuration is defined by at least one of:
    a table angle of a table for placement of the patient,
    a vertical angle of a gantry of an irradiation device for irradiating the anatomical structure with the ionizing radiation,
    a collimator angle of a collimator for collimating the beam of ionizing radiation to be emitted by the irradiation device,
    a jaw configuration of the irradiation device, and
    monitor units per control point.

7. The method according to claim 1, wherein the changed irradiation dose distribution is an optimized irradiation dose distribution.

8. The method according to claim 1, further comprising:
determining, by the at least one processor and based on the changed dose distribution data, treatment plan data describing a treatment plan for conducting the medical procedure.

9. The method according to claim 1, wherein the medical image data has been generated by application of a medical imaging modality to a specific patient or wherein the medical image data is atlas data describing an image-based model of the anatomical structure.

10. A non-transitory computer-readable storage medium having instructions stored thereon for determining a dose distribution for use in a medical procedure involving irradiation of an anatomical structure of a patient's body with ionizing radiation, which, when executed, cause a computer system to perform the steps comprising:
   a) acquiring, at the at least one processor, medical image data describing a medical image of the anatomical structure, the medical image comprising a plurality of image units, wherein the anatomical structure comprises both a target region which defines a target of the irradiation and non-target tissue;
   b) acquiring, at the at least one processor, dose distribution data describing an irradiation dose distribution of the anatomical structure, as spatially defined in a reference system of the medical image of the anatomical structure;
   c) acquiring, at the at least one processor and based on the medical image data, tissue index contribution data, wherein said tissue index contribution data describes, for each image unit of the medical image of the anatomical structure describing non-target tissue, a contribution of the irradiation dose assigned to that image unit to at least one tissue index said tissue index describing a quality of the irradiation dose distribution wherein said at least one tissue index is at least one of:
      i) a conformity index CI which is associated with the dose distribution data and the medical image data and which is defined as CI=(volume of the target region*volume of the target region or the non-target tissue having an assigned irradiation dose larger than 100% of the prescribed dose)/(volume of the target region having an assigned irradiation dose larger than 100% of the prescribed dose)$^2$, where * is the arithmetic operator of multiplication and/is the arithmetic operator of division; and
      ii) a gradient index GI which is associated with the dose distribution data and the medical image data and which is defined as GI=(volume of the target region or the non-target tissue having an assigned irradiation dose larger than a predetermined percentage of the prescribed dose)/(volume of the target region or the non-target tissue having an assigned irradiation dose larger than 100% of the prescribed dose);
   d) determining prioritization data by the at least one processor, said prioritization data based on the medical image data, and the dose distribution data, wherein and the tissue index contribution data, wherein said prioritization data describes, for each image unit describing non-target tissue, a priority of that image unit for consideration during an optimization of the irradiation dose distribution described by the dose distribution data; and
   e) determining changed dose distribution data by the at least one processor, said changed dose distribution data based on the dose distribution data and the prioritization data, and wherein said changed dose distribution data describing a changed irradiation dose distribution spatially defined in the reference system of the medical image of the anatomical structure, wherein the changed irradiation dose distribution is comprised in the output of at least a step of an optimization algorithm, said optimization algorithm having the dose distribution data and the prioritization data as an input.

11. A system for use in a medical procedure involving irradiation of an anatomical structure with ionizing radiation, the system comprising at least one processor, a memory, and an irradiation therapy device, and wherein the processor is configured to:
   a) acquire from the memory medical image data describing a medical image of the anatomical structure, the medical image comprising a plurality of image units, wherein the anatomical structure comprises both a target region which defines a target of the irradiation and non-target tissue;
   b) acquire, from the memory, dose distribution data describing an irradiation dose distribution of the anatomical structure, as spatially defined in a reference system of the medical image of the anatomical structure;
   c) acquire, based on the medical image data, tissue index contribution data, wherein said tissue index contribution data describes, for each image unit of the medical image of describing non-target tissue, a contribution of the irradiation dose assigned to that image unit to at least one tissue index, said tissue index describing a quality of the irradiation dose distribution, wherein said at least one tissue index is at least one of:
      i) a conformity index CI which is associated with the dose distribution data and the medical image data and which is defined as CI=(volume of the target region*volume of the target region or the non-target tissue having an assigned irradiation dose larger than 100% of the prescribed dose)/(volume of the target region having an assigned irradiation dose larger than 100% of the prescribed dose)$^2$, where * is the arithmetic operator of multiplication and/is the arithmetic operator of division; and
      ii) a gradient index GI which is associated with the dose distribution data and the medical image data and which is defined as GI=(volume of the target region or the non-target tissue having an assigned irradiation dose larger than a predetermined percentage of the prescribed dose)/(volume of the target region or the non-target tissue having an assigned irradiation dose larger than 100% of the prescribed dose);
   d) determine prioritization data, said prioritization data based on the medical image data, the dose distribution data and the tissue index contribution data, wherein said prioritization data describes for each image unit describing non-target tissue, a priority of that image unit for consideration during an optimization of the irradiation dose distribution described by the dose distribution data;
   e) determine changed dose distribution data, said changed dose distribution data based on the dose distribution data and the prioritization data, wherein said changed dose distribution data describes a changed irradiation dose distribution spatially defined in the reference system of the medical image of the anatomical structure, and wherein the changed irradiation dose distribution is comprised in the output of at least a step of an optimization algorithm, said optimization algorithm having the dose distribution data and the prioritization data as an input; and f) effect emission of the treatment radiation by the irradiation therapy device based on the changed dose distribution data.

12. The system of claim 11, wherein the priority defines, for a dose value associated with each image unit, an influence on determining a desired changed irradiation dose distribution by applying the optimization algorithm, and wherein the influence is represented by a numeric value which correlates with the contribution of the image unit to an optimization result.

13. The system of claim 11, wherein the contribution of the irradiation dose assigned to each image unit is defined based on prior knowledge.

14. The system of claim 11, wherein the tissue index includes both the conformity index and the gradient index and wherein determining the changed dose distribution data involves minimizing the conformity index and the gradient index.

15. The system of claim 11, wherein the prioritization data is determined based on determining the result of $|D_i^{desired} - D_i^{actual}(\omega)|$ or $(D_i^{desired} - D_i^{actual}(\omega))^2$, where $D_i^{desired}$ is a desired irradiation dose to be applied to the non-target tissue represented by the i-th image unit, and $D_i^{actual}(\omega)$ is the irradiation dose to be applied to the non-target tissue represented by the i-th image unit and described by the dose distribution data and is dependent on a machine configuration $\omega$, wherein $D_i^{desired}$ is set such that image units associated with a higher priority are associated with a higher value of $|D_i^{desired} - D_i^{actual}(\omega)|$ or $(D_i^{desired} - D_i^{actual}(\omega))^2$, respectively, and wherein, for a high-priority image unit, $D_i^{desired}$ is set to $D_i^{desired} = a_i D_i^{actual}(\omega)$ and for a low-priority image unit $D_i^{desired}$ is set to $D_i^{desired} = b_i D_i^{actual}(\omega)$, where $0 < a_i < b_i < 1$.

16. The system of claim 11, wherein the changed dose distribution data is determined based on minimizing a cost function $f(\omega) = f_0(\omega) + f_1(\omega)$, where $f_1(\omega)$ describes the part of the cost function for the non-target tissue and is defined as $f_1(\omega) = \Sigma_i p_i [D_i^{desired} - D_i^{actual}(\omega)]^2$, where $f_0(\omega)$ describes the part of the cost function for parts of the anatomical structure other than the non-target tissue and irradiation parameters, where $\omega$ is a parameter defining the configuration of the irradiation therapy device, where $p_i$ is a numeric value defining the priority of the i-th image unit describing non-target tissue and assigned to the i-th image unit based on prior knowledge, where $D_i^{desired}$ is a desired irradiation dose to be applied to the non-target tissue represented by the i-th image unit, where $D_i^{actual}(\omega)$ is the irradiation dose to be applied to the non-target tissue represented by the i-th image unit and described by the dose distribution data and is dependent on the irradiation therapy device configuration $\omega$, and wherein the irradiation therapy device configuration is defined by at least one of:

a table angle of a table for placement of the patient, a vertical angle of a gantry of the irradiation therapy device, a collimator angle of a collimator for collimating the beam of ionizing radiation to be emitted by the irradiation therapy device, a jaw configuration of the irradiation therapy device, and monitor units per control point.

* * * * *